(12) United States Patent
Neurohr et al.

(10) Patent No.: US 12,114,957 B2
(45) Date of Patent: Oct. 15, 2024

(54) MEDICAL APPARATUS WITH GALVANIC ISOLATOR

(71) Applicant: Richard Wolf GmbH, Knittlingen (DE)

(72) Inventors: Bernd Neurohr, Oberderdingen/Grossvillars (DE); Robert Send, Karlsruhe (DE)

(73) Assignee: RICHARD WOLF GMBH, Knittlingen (DE)

( * ) Notice: Subject to any disclaimer, the term of this patent is extended or adjusted under 35 U.S.C. 154(b) by 0 days.

(21) Appl. No.: 18/065,029

(22) Filed: Dec. 13, 2022

(65) Prior Publication Data
US 2023/0181036 A1    Jun. 15, 2023

(30) Foreign Application Priority Data
Dec. 14, 2021 (DE) .................. 20 2021 106 775.6

(51) Int. Cl.
*A61B 5/00* (2006.01)
*H02J 50/05* (2016.01)
(Continued)

(52) U.S. Cl.
CPC ............ *A61B 5/0015* (2013.01); *H02J 50/05* (2016.02); *H02J 50/10* (2016.02); *H04B 5/72* (2024.01);
(Continued)

(58) Field of Classification Search
CPC .............. A61B 5/0015; A61B 1/00018; A61B 1/00029; A61B 1/00114; A61B 2560/0214; A61B 2562/225; A61B 5/0026; H02J 50/05; H02J 50/10; H02J 2310/23; H04B 5/72; H05K 1/0243; H05K 1/142;
(Continued)

(56) References Cited

U.S. PATENT DOCUMENTS

| 2015/0115407 A1* | 4/2015 | Tao ................... H01L 29/66181 257/532 |
| 2017/0133841 A1* | 5/2017 | Coyne ................ H01L 29/8083 |

(Continued)

FOREIGN PATENT DOCUMENTS

| JP | 2010183055 A | 8/2010 |
| JP | 2014514894 A | 6/2014 |

(Continued)

*Primary Examiner* — Amine Benlagsir
(74) *Attorney, Agent, or Firm* — McGlew and Tuttle, P.C.

(57) ABSTRACT

A medical apparatus having an application device which can be brought into contact with a patient to be treated, and a galvanic isolator which can be connected to the application device, the isolator having at least one application connector for connection to the application device and at least one supply connector for connection to a device. The isolator is configured to galvanically isolate the application connector from the supply connector. The isolator has at least one first radio unit connected to the application connector, and at least one second radio unit connected to the supply connector. The first antenna and second antenna are fixed on a carrier at a visible distance from each other. The at least one first radio unit and the at least one second radio unit are configured to transmit signals and/or data between the application connector and the supply connector.

16 Claims, 7 Drawing Sheets

(51) Int. Cl.
   *H02J 50/10*    (2016.01)
   *H04B 5/72*    (2024.01)
   *H05K 1/02*    (2006.01)
   *H05K 1/14*    (2006.01)

(52) U.S. Cl.
   CPC .......... *H05K 1/0243* (2013.01); *H05K 1/142* (2013.01); *H02J 2310/23* (2020.01); *H05K 2201/1003* (2013.01); *H05K 2201/10098* (2013.01)

(58) Field of Classification Search
   CPC . H05K 2201/1003; H05K 2201/10098; H05K 9/0009; H01F 27/2804; H01F 38/14; H01F 2038/143; H04L 25/0266; G08C 17/02; H01Q 1/526; H04W 4/80
   See application file for complete search history.

(56) References Cited

U.S. PATENT DOCUMENTS

| | | | |
|---|---|---|---|
| 2018/0040941 A1* | 2/2018 | Lee | H01Q 1/38 |
| 2018/0219334 A1 | 8/2018 | Kahlman | |
| 2019/0372276 A1* | 12/2019 | Kahlman | H04B 5/72 |
| 2021/0119670 A1* | 4/2021 | Lambkin | H04L 25/0266 |

FOREIGN PATENT DOCUMENTS

| | | |
|---|---|---|
| JP | 2018534894 A | 11/2018 |
| JP | 2020110307 A | 7/2020 |

* cited by examiner

MEDICAL APPARATUS WITH GALVANIC ISOLATOR

CROSS REFERENCE TO RELATED APPLICATIONS

This application claims the benefit of priority under 35 U.S.C. '119 of German Application 20 2021 106 775.6, filed Dec. 14, 2021, the entire contents of which are incorporated herein by reference.

TECHNICAL FIELD

The present invention relates to a medical apparatus with an application device which can be brought into contact with a patient to be treated and a galvanic isolator which can be connected to the application device having medical device features.

TECHNICAL BACKGROUND

For medical apparatuses that operate with potentially hazardous voltages ("PHV"), it must be ensured that no direct, electrically conductive connection exists between a voltage source and the patient. For endoscopic cameras, for example, it is envisaged that at least one galvanic isolating element is provided between a power supply and an endoscopic optical unit to prevent a direct, electrically conductive connection. The IEC60601 1 standard, among others, specifies requirements for clearances and creepage distances, dielectric strength and possible leakage currents through a patient. The implementation of electromagnetic shielding or compatibility with respect to radiation and emission of electromagnetic interference is particularly demanding for electrical devices with galvanic isolation and is associated with higher manufacturing and development costs. One challenge is, among other things, that not all electronic components can be connected to the same ground specified by the power supply network, which is usually used for shielding. Thus, even the connection of a low-voltage device, such as a commercially available computer mouse, could lead to undesired interference radiation.

In addition to a galvanic isolation function, there is often the requirement to transmit large amounts of data. Although there are components that can transmit data over galvanic isolation paths, these are costly or their achievable data rates are clearly limited.

SUMMARY

An object of the invention is to provide a medical apparatus in which an easy-to-implement and yet effective galvanic isolation is made possible, which allows high data rates, can be produced cost effectively and also can be easily checked.

This object is achieved in accordance with the invention by a medical apparatus having the features described. Advantageous embodiments of the invention are indicated in the following description, and the drawings.

The medical apparatus according to the invention comprises an application device which can be brought into contact with a patient to be treated, and a galvanic isolator which can be connected to the application device, the isolator comprising at least one application connector for connection to the application device and at least one supply connector for connection to a device, the isolator being configured to galvanically isolate the application connector from the supply connector. According to the invention, it is provided that the isolator comprises at least one first radio unit connected to the application connector and having a first antenna, and at least one second radio unit connected to the supply connector and having a second antenna, each first antenna and each second antenna being fixed on a carrier at a distance from each other which is visible to the naked eye and preferably facing each other, and the at least one first radio unit and the at least one second radio unit being configured to transmit signals and/or data between the application connector and the supply connector.

The feature that each first antenna and each second antenna are spaced from each other on a carrier visibly "with the naked eye" can mean here, for example, that for the detection of the distance between the antennas, they do not have to be removed for microscopic examination. Typically, this already applies to distances above 0.5 mm. Preferably, however, the distance between the antennas is at least 0.5 cm, which can be detected with the naked eye with normal visual acuity and without any optical aid. Preferably, the spacing is arranged so as to be freely visible and not concealed, i.e. directly visible when the apparatus is inspected without prior removal of parts, apart from any opening of a housing of the apparatus. Preferably, each first antenna and each second antenna are fixed facing each other. This is to be understood, for example, in such a way that the first antenna defines a first main radio direction for transmitting and/or receiving radio signals and the second antenna defines a second main radio direction for transmitting and/or receiving radio signals, the first main radio direction being oriented coaxially opposite to the second main radio direction.

The application device can be embodied in many different ways. For example, it could include an endoscope apparatus and/or a sensor, electrodes, imagers, ultrasonic transducers and the like. The application device can enable the provision of signals and/or data due to its particular design. Any other devices are conceivable which can be brought directly into contact with a patient and in which a galvanic isolator can be integrated. On the other hand, the galvanic isolator could also be integrated into a component that can be connected to an application device, for example a processing unit. For example, the galvanic isolator could also allow data or signal transmission between directly adjacent pieces of equipment. The pieces of equipment could have metal housings with a recess through which signal and/or data transmission takes place. Consequently, if the pieces of equipment are correctly oriented relative to each other, data transmission could be realized. Orientation could be facilitated by guides, indentations or magnets. A galvanic isolator could be integrated for example into a housing base on one side.

The galvanic isolator is used to transmit signals and/or data between the application device and a device that is to be connected to the application device. The isolator thus forms an interface that allows electrically safe operation of the application device on the patient.

A special feature lies the use of the at least one first radio unit and the at least one second radio unit, which are each connected to an antenna and are spaced apart from each other on the carrier in a manner visible to the naked eye. A mechanical and electrical isolation between two galvanically isolated areas is therefore completely obvious without extensive testing and therefore can be easily verified. Consequently, approval for a medical apparatus can be obtained without a technically complex test as is required for the aforementioned prior art apparatuses.

The radio-based connection can be established via a short-range radio with low radio power. It is conceivable to realize a radio power in a range of from 0.01 W to 300 mW and in particular from 0.02 W to 193 mW. Corresponding modules are known for data transmission. Short-range radio can operate in the GHz range, for example in the 60 GHz V-band with radio frequencies in the 57 GHz and 64 GHz range. This has the advantage that the transmission can easily be shielded by metal layers. Consequently, the galvanic isolator itself does not emit any interfering radiation when it is surrounded by a conductive housing.

A gap between the first antenna and the second antenna functions as an isolation gap or radio path. The gap can be formed in such a way that at least the usual standards for clearance and creepage distances are met. It may be filled with air only, but may also contain certain materials, such as plastics and in particular a printed circuit board material.

It is preferred if a particularly preferably two-phase switch and/or a preferably two-phase device fuse is additionally provided at the supply connector.

The isolator could comprise two first radio units and two second radio units, the first radio units and the second radio units facing each other in pairs, and one of the pairs being configured to transmit signals and/or data from the first radio unit to the second radio unit and the other of the pairs being configured to transmit signals and/or data from the second radio unit to the first radio unit. Consequently, the isolator can implement a duplex transmission, in which signals and/or data can be transmitted in two directions. In this case, signals and/or data can be transmitted in both directions simultaneously.

The at least one first radio unit and the at least one second radio unit could each be embodied as a transmitting and receiving unit. The signal and/or data transmission can therefore basically take place in both directions. If there is only a single pair consisting of a first radio unit and a second radio unit, a semi-duplex connection can be realized.

A radio path present between the first antenna and the second antenna could have an extent of from 0.5 to 60 cm and particularly preferably of from 1 to 40 cm. The extent of the radio path over a distance of at least 0.5 cm is very easy to see with the naked eye. This significantly simplifies the checking of the isolator. An extent specified here with a maximum of 60 cm can significantly limit the necessary radio power. Especially in the case of strong directionality of the antennas, both an effective galvanic isolation and a minimisation of the radio power can be achieved.

The carrier could be embodied as a single circuit board on which the at least one first radio unit and the at least one second radio unit are mounted at a predetermined distance from each other. This is particularly simple mechanically, as the first radio unit and the second radio unit or their antennas only need to be attached to designated positions on the circuit board to establish the desired radio connection. The shape of the carrier is also very easily adaptable to the medical apparatus and could in particular be integrated into the application device.

The circuit board could comprise a recess between the first radio unit and the second radio unit. The recess could serve to achieve an even further improved visual inspection of the galvanic isolation. In particular, the recess could have a rectangular cut out that is visible to the naked eye and represents an isolation between the first radio unit and the second radio unit. The antennas are preferably arranged at the edges of the recess opposite each other and thus form their radio path above the recess.

The carrier could comprise a first circuit board and a second circuit board, which are arranged at a predetermined distance from each other and are mechanically connected to each other, the at least one first radio unit being arranged on the first circuit board and the at least one second radio unit being arranged on the second circuit board. Particularly in the case of larger or longer medical apparatuses, it may be useful to use, instead of a single circuit board, two separate circuit boards which are mechanically arranged and fastened at a predetermined distance from one another. For example, it may be convenient to arrange one circuit board at a distal end of the application device and to offset the other circuit board towards a proximal end. The application device can comprise a housing that encloses the two circuit boards and has fastening points inside that allow the circuit boards to be fastened.

The first antenna and the second antenna could be printed on the carrier. Printing could be achieved by applying and fixing conductive particles, by etching or another manufacturing process. This results in a particularly easy-to-manufacture isolator that is cost-effective and spatially compact. This allows in particular a realization in application devices with a small cross-section.

Furthermore, the first antenna and the second antenna could each comprise a horn structure for establishing a directional radio connection. The horn structure supports the strong directional character of the antennas. The data rates can be increased in this case. It is conceivable to realize multi-link applications in which two different horn structures with vertical and horizontal polarization are used to increase the data rates even further. In addition to horn structures, horn antennas with an integrated antenna could also be used.

The isolator could comprise a first coupling unit connected to the application connector and a second coupling unit connected to the supply connector, which are configured to inductively and/or capacitively transmit electrical power from the supply connector to the application connector. Consequently, the two coupling units allow electrical power to be transmitted wirelessly. Thus, a distally arranged lighting device, a sensor device or any other type of consumer could be supplied with electrical power without requiring a direct connection between the supply connector and the application device. It is particularly suitable here to implement an inductive transmission comprising two coils that can be coupled to each other. The two coils can be brought into alignment so that a voltage applied to the supply connector is induced in a corresponding coil connected to the application device.

The isolator could be enclosed by a housing. The housing could be a separate housing that can be placed inside the application device. It is also conceivable to enclose the isolator by a housing in such a way that the radio link between the antennas is visible from the outside. It is conceivable, for example, to fill the housing with a transparent, non-conductive plastic. The housing could also be a housing associated with the application device, in which only the isolator is arranged and does not necessarily comprise its own separate housing.

A housing surrounding all or part of the radio link could be metal conductive, with conductivities greater than 0.0004 S/m, to provide electromagnetic shielding. The housing could further be a plastic housing. The preferred wall thickness may exceed 0.5 mm and may be, for example, up to about 3 mm. It is particularly preferred to provide a chemical resistance of a housing surface to alcohols, aldehydes, water and surfactants to achieve good cleanability.

It is advantageous if a ratio v=d/L between a distance d between the at least one first radio unit and the at least one second radio unit and a wavelength L of the signals lies in a range of from 1.73 to 127. In this way, an excellent signal and/or data transmission can be realized.

An area between the at least one first radio unit and the at least one second radio unit could be at least partially filled with a material having a permittivity of from 1 to 23 F/m and a conductivity of from 0 to 0.01 S/m. Particularly preferably, this could be air, a plastic, or circuit board material.

The area can further preferably be filled with media of which the absorption coefficient I/I0 for light in the range 400 nm-750 nm along the radio path does not exceed the value 0.7.

The isolator is preferably configured in such a way that the attenuation of the transmission power at room temperature and normal pressure is between 0.01 and 10 dB/km.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
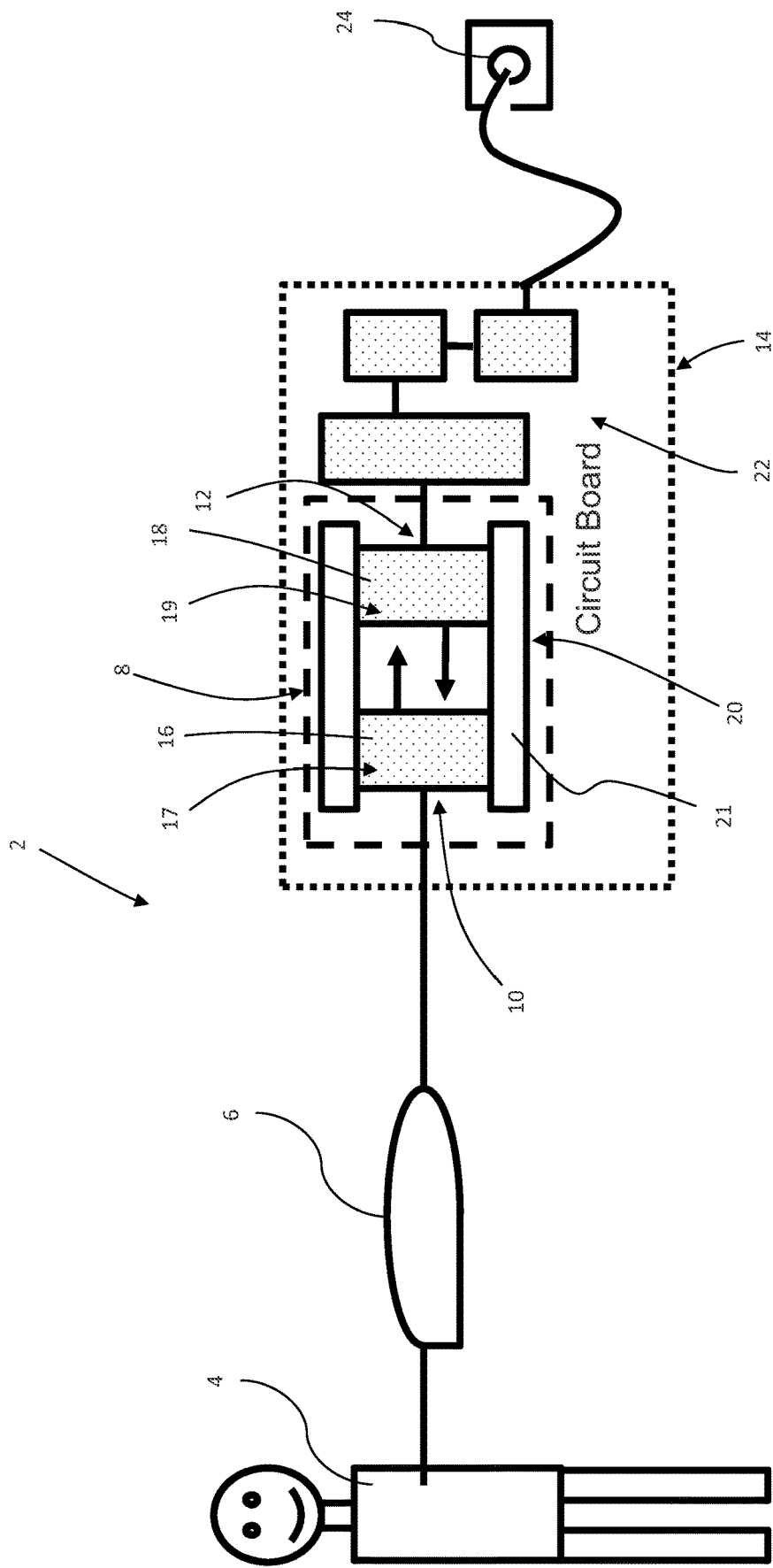
FIG. 1 is a schematic overview of the medical apparatus.

Referring to the drawings, FIG. 1 shows a medical apparatus 2 for treating a patient 4. The medical apparatus 2 comprises an application device 6 which can be brought into contact with the patient 4. A galvanic isolator 8, which can be connected to the application device 6, is shown very schematically. The isolator 8 comprises an application connector 10 for connection to the application device 6 and a supply connector 12 for connection to a device 14. The isolator 8 is configured to galvanically isolate the application connector 10 from the supply connector 12. Here, the isolator 8 is embodied as part of the device 14. However, it is also conceivable that the isolator 8 is part of the application device 6.

The isolator 8 comprises a first radio unit 16 connected to the application connector 10 and a second radio unit 18 connected to the supply connector 12. The first radio unit 16 comprises a first antenna 17, while the second radio unit 18 comprises a second antenna 19. The isolator 8 is shown here only schematically, and therefore no exact antenna structure can be seen in this illustration. This is shown in more detail in the following figures.

The first antenna 17 and the second antenna 19 are spaced apart on a carrier 20 in a manner visible to the naked eye and are directed towards each other. As a result, the first radio unit 16 and the second radio unit 18 are configured to transmit signals and/or data between the application connector 10 and the supply connector 12. There is no direct electrical connection between the application connector 10 and the supply connector 12.

An exemplary arrangement of circuit boards 22 is provided at the supply connector 12, the circuit boards being connected to a voltage source 24 and supplying the supply connector 12 with a corresponding voltage or electrical power. The patient 4, however, is not in direct contact with the voltage source 24 due to the galvanic isolator 8.

The first radio unit 16 and the second radio unit 18 are each embodied as a circuit board, these being connected to each other by means of mechanical fixings 21. The circuit boards and the fixings 21 thus form the carrier 20.

Figure 2:
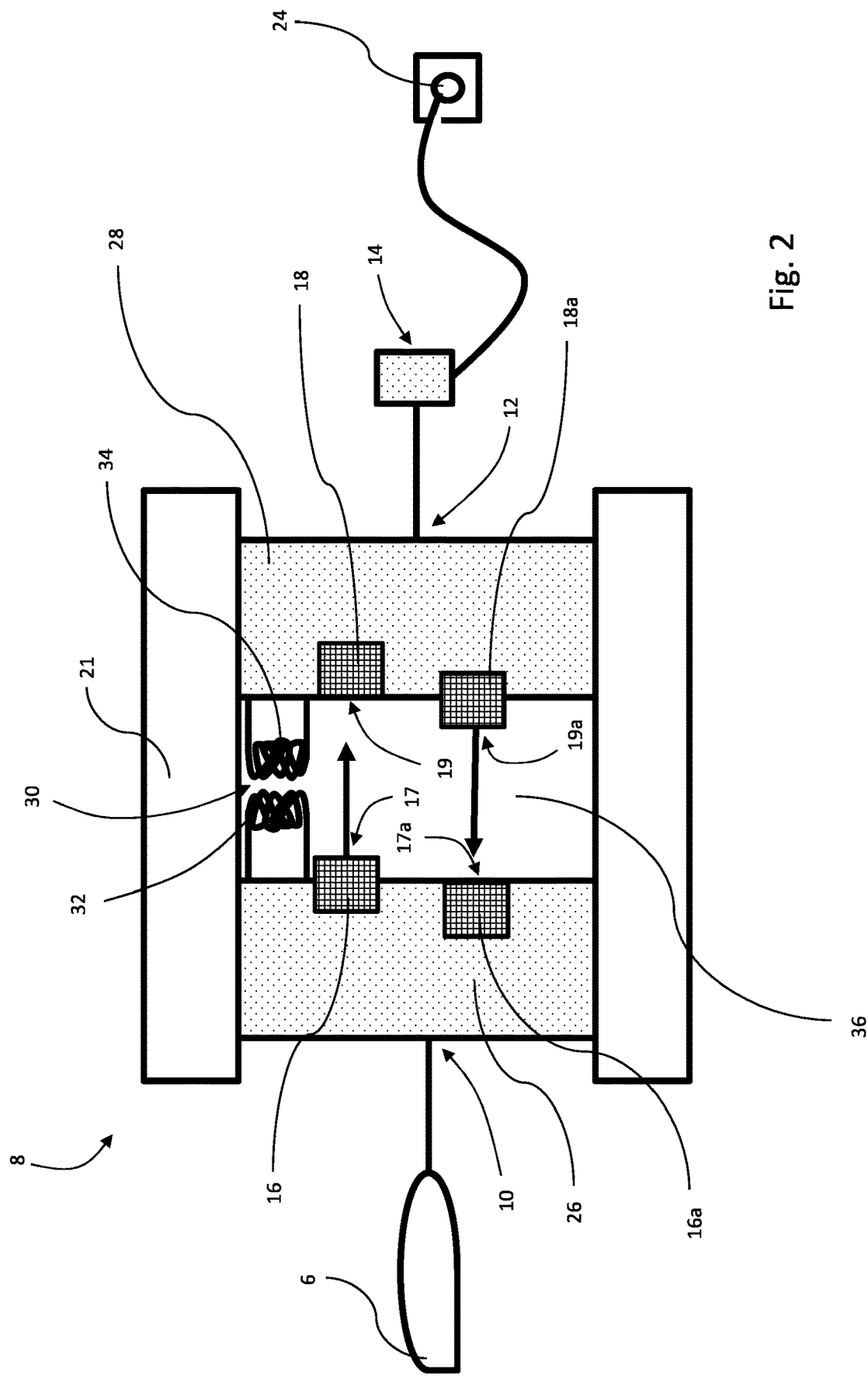
FIG. 2 is a schematic representation of a galvanic isolator.

FIG. 2 shows an exemplary embodiment of the galvanic isolator 8 in a somewhat more detailed representation. A first circuit board 26 with a first radio unit 16 arranged thereon is shown here. The first antenna 17 is oriented here to the right in the drawing plane and points there towards the second antenna 19 of the second radio unit 18, which in turn is arranged on a second circuit board 28. A further first radio unit 16a is arranged on the first circuit board 26 and has a further first antenna 17a. A second antenna 19a is directed towards this antenna and is assigned to a further second radio unit 18a. Through this arrangement, a bidirectional radio connection between the supply connector 12 and the application connector 10 can be realized even when using two unidirectional first radio units 16 and 16a as well as two unidirectional second radio units 18 and 18a.

In addition thereto, a coupling device 30 is provided which comprises a first coupling unit 32 and a second coupling unit 34. Both are embodied as coils which are aligned with each other and are configured to transmit electrical power wirelessly from the supply connector 12 to the application connector 10.

Between the two circuit boards 26 and 28, an isolation gap 36 or radio path 36 is provided, which is visible to the naked eye and has an extent of at least 0.5 cm. The radio units 16, 16a, 18 and 18a as well as the coupling units 32 and 34 transmit signals and/or data and an electrical power wirelessly via this isolation gap 36, so that there is galvanic isolation. The mechanical fixings 21 are non-conductive. They can be made for example from a printed circuit board material, plastic, or another non-conductive material and only allow a favorable fixing of the components to each other.

Figure 3:
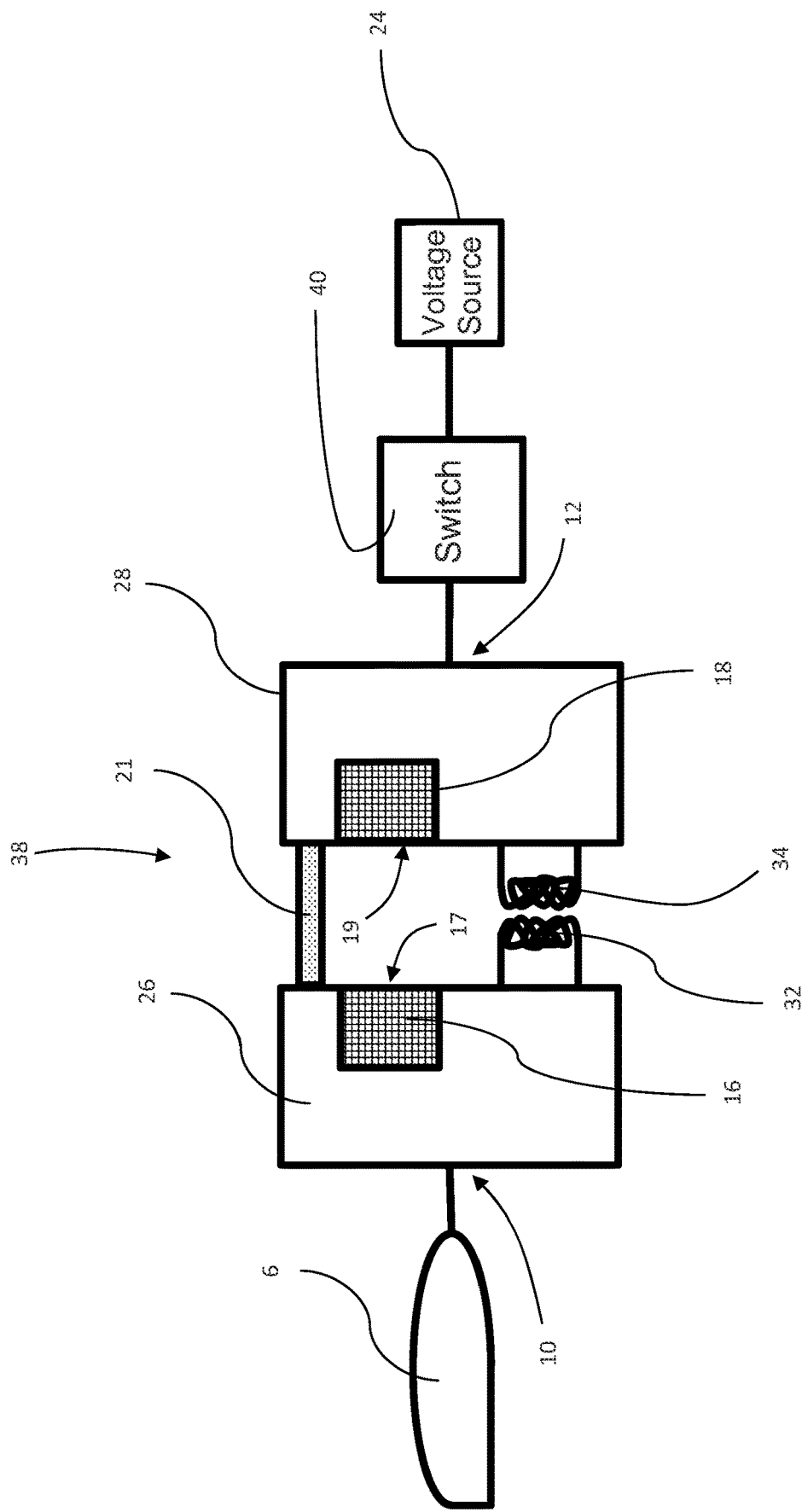
FIG. 3 is a schematic representation of a galvanic isolator.

FIG. 3 shows a modification in the form of a galvanic isolator 38 in which only a single first radio unit 16 and a single second radio unit 18 are provided. These can operate bidirectionally by way of example and consequently permit bidirectional communication in a simpler arrangement. Only by way of example, a switch 40 is provided which is connected to the voltage source 24 and to the supply connector 12.

Figure 4:
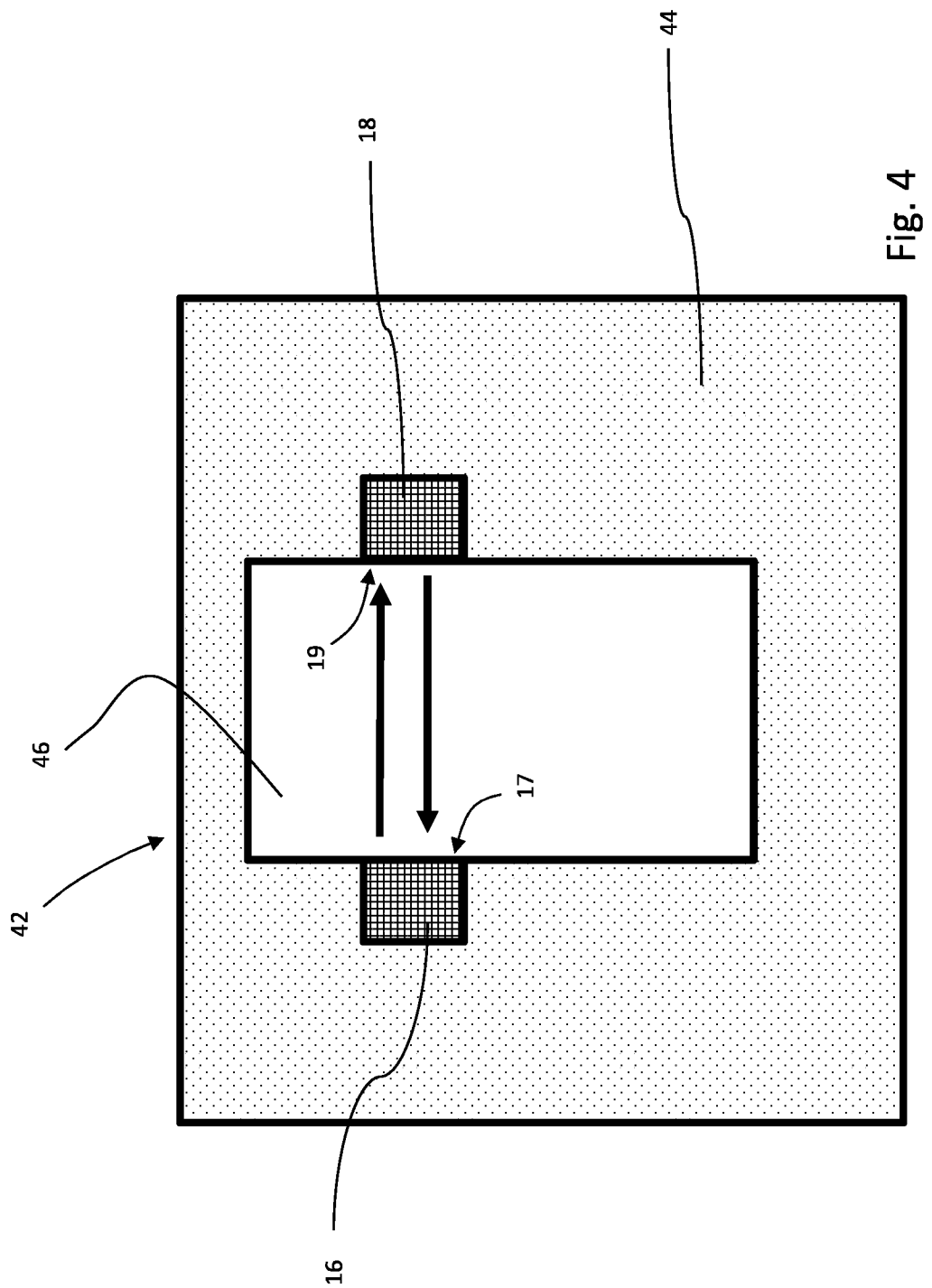
FIG. 4 is a schematic representation of a galvanic isolator.

FIG. 4 schematically shows a galvanic isolator 42 in which a first radio unit 16 and a second radio unit 18 can communicate bidirectionally and are arranged on a single circuit board 44. This has a cut-out 46, which is visually perceptible, above the isolation gap 36.

Figure 5:
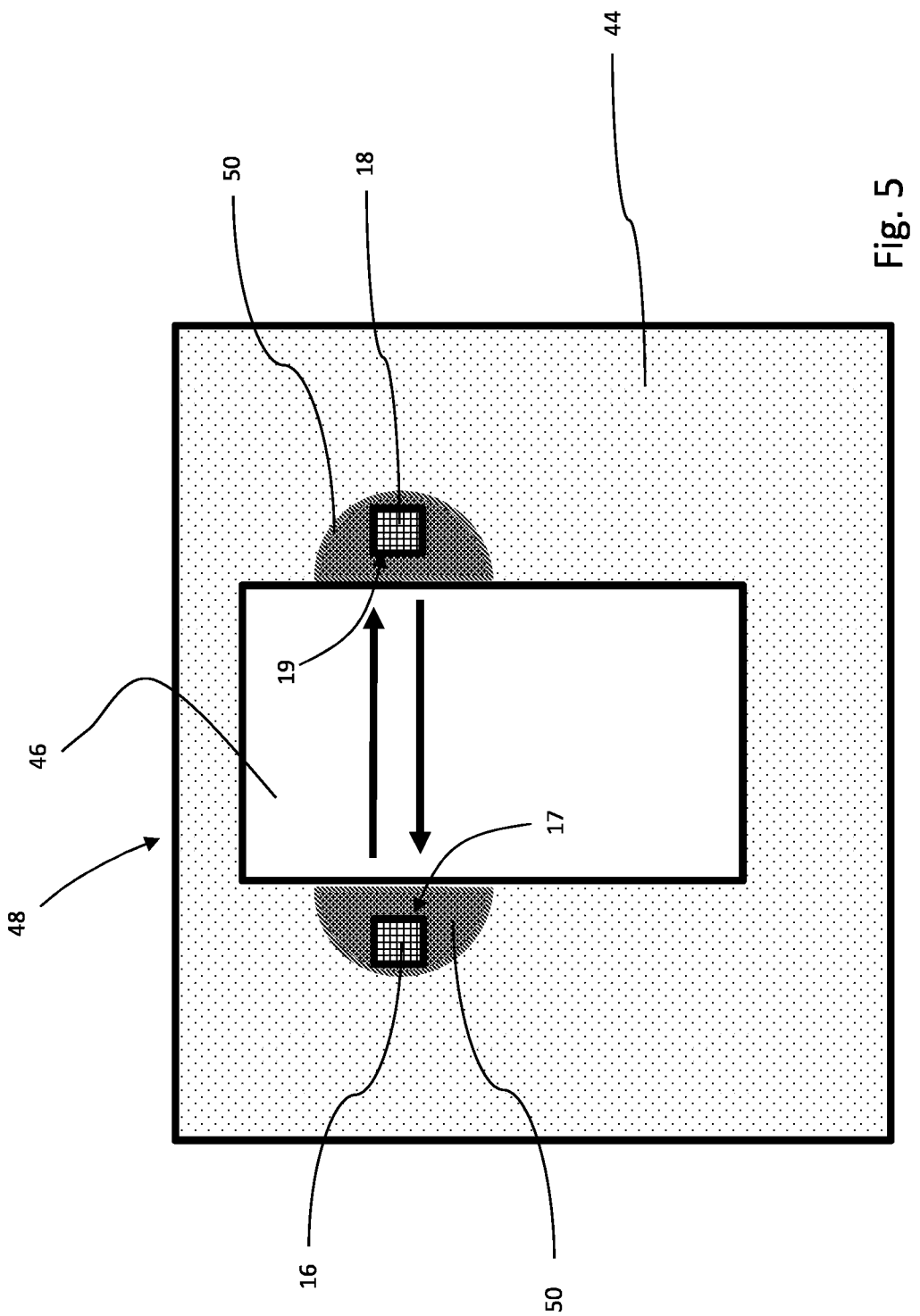
FIG. 5 is a schematic representation of a galvanic isolator.

FIG. 5 shows a galvanic isolator 48, which is based on the isolator 42 from FIG. 4. Here, horn structures 50 are provided and are arranged one on the first radio unit 16 and one on the second radio unit 18. Both horn structures 50 serve to orient the radio waves that emanate from the radio units 16 and 18. In this way, higher data rates can be realized with a simultaneous reduction of the radio power.

Figure 6:
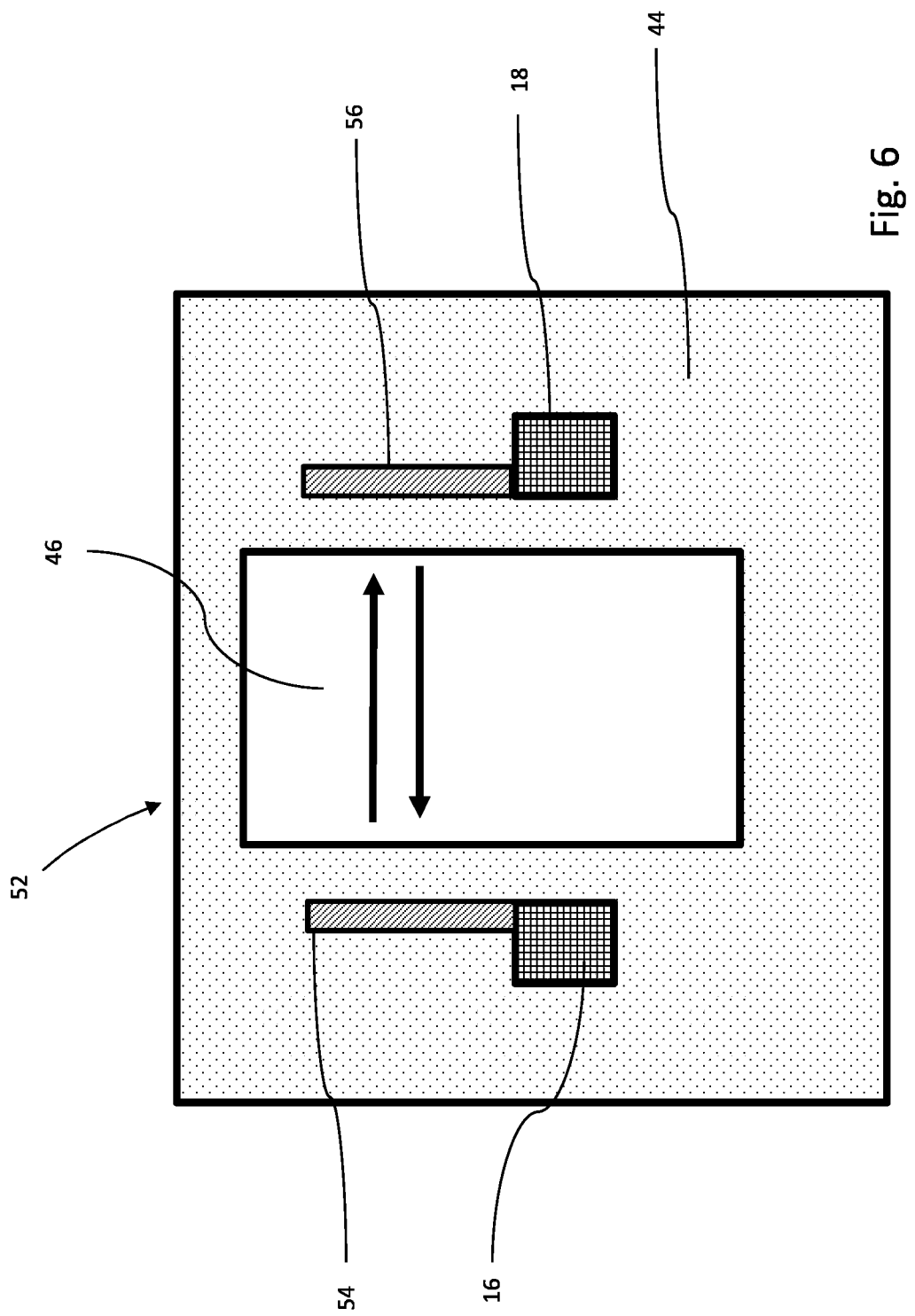
FIG. 6 is a schematic representation of a galvanic isolator.

Alternatively, a galvanic isolator 52 according to FIG. 6 could also comprise printed antennas 54 or 56 arranged at the edge of the gap 36 and aligned with each other.

Figure 7:
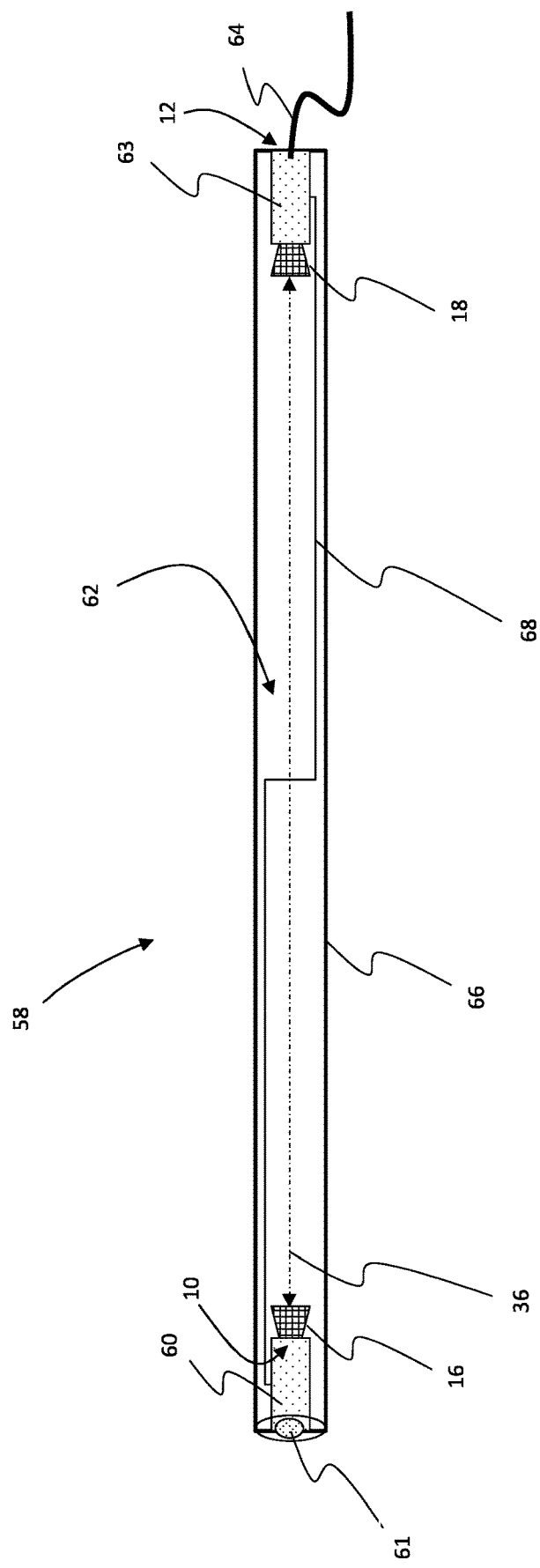
FIG. 7 is a schematic representation of an application device.

FIG. 7 shows an application device 58 in the form of an endoscope. Here, a distal electronic device 60, for example, an imager with an optical unit 61 arranged thereon, is arranged in a distal end and is coupled to a proximally arranged supply connector 12 via a galvanic isolator 62. A proximal electronic device 63 is provided directly at the supply connector 12 and is directly connectable to a voltage connector or a processing unit via a cable 64. The application device 58 may have a long length, up to about 60 cm. In this exemplary embodiment, the isolation gap 36 may extend over a substantial portion of this length and consequently may be up to about 60 cm. The application device 58 may comprise a housing 66 which is at least partially made of a metal material. A line 68 for supplying power to the distal electronic unit 60 may be connected to a coupling device 30 which is integrated in the proximal electronic unit 63 or an external processing unit.

While specific embodiments of the invention have been shown and described in detail to illustrate the application of the principles of the invention, it will be understood that the invention may be embodied otherwise without departing from such principles.

LIST OF REFERENCE SIGNS 2 medical apparatus
4 patient
6 application device
8 isolator
10 application connector
12 supply connector
14 device
16, 16a first radio unit
17, 17a first antenna
18, 18a second radio unit
19, 19a second antenna
20 carrier
21 mechanical fixing
22 circuit board
24 voltage source
26 first circuit board
28 second circuit board
30 coupling device
32 first coupling unit
34 second coupling unit
36 isolation gap
38 galvanic isolator
40 switch
42 galvanic isolator
44 single circuit board
46 cut-out
48 galvanic isolator
50 horn structure
52 galvanic isolator
54 printed first antenna
56 printed second antenna
58 application device
60 electronic device
61 optical unit
62 galvanic isolator
63 proximal electronic device
64 cable
66 housing
68 line

What is claimed is:

1. A medical apparatus comprising:
    an application device which can be brought into contact with a patient to be treated, and
    a galvanic isolator which can be connected to the application device, the galvanic isolator comprising:
    at least one application connector for connection to the application device; and
    at least one supply connector for connection to a device, the galvanic isolator being configured to galvanically isolate the at least one application connector from the at least one supply connector;
    at least one first radio unit connected to the at least one application connector, the at least one first radio unit having a first unit antenna;
    at least one second radio unit connected to the at least one supply connector and having a second unit antenna;
    a carrier,
    wherein: the first unit antenna and the second unit antenna is fixed on the carrier at a visible distance from each other, the first unit antenna and the second unit antenna being fixed facing each other; and the at least one first radio unit and the at least one second radio unit is configured to transmit signals and/or data between the at least one application connector and the at least one supply connector.

2. The medical apparatus according to claim 1, wherein the galvanic isolator further comprises another first radio unit to provide two first radio units and comprises another second radio unit to provide two second radio units, the two first radio units and the two second radio units facing each other in pairs, and one of the pairs being configured to transmit first signals and/or first data from one of the two first radio units to one of the two second radio units and another of the pairs being configured to transmit second signals and second data from the other second radio unit of the two second radio units to the other first radio unit of the two first radio units.

3. The medical apparatus according to claim 1, wherein the at least one first radio unit and the at least one second radio unit are each embodied as a transmitting and receiving unit.

4. The medical apparatus according to claim 1, wherein a radio path present between the first unit antenna and the second unit antenna has an extent of from 0.5 to 60 cm.

5. The medical apparatus according to claim 1, wherein the carrier is embodied as a single circuit board on which the at least one first radio unit and the at least one second radio unit are mounted at a predetermined distance from each other.

6. The medical apparatus according to claim 5, wherein the circuit board comprises a recess between the at least one first radio unit and the at least one second radio unit.

7. The medical apparatus according to claim 1, wherein the carrier comprises:
    a first circuit board; and
    a second circuit board, the first circuit board and the second circuit board being arranged at a predetermined distance from each other, the at least one first radio unit being arranged on the first circuit board and the at least one second radio unit being arranged on the second circuit board.

8. The medical apparatus according to claim 1, wherein the first unit antenna and the second unit antenna are printed on the carrier.

9. The medical apparatus according to claim 1, wherein the first unit antenna and the second unit antenna each comprise a horn structure for establishing a directional radio connection.

10. The medical apparatus according to claim 1, wherein the galvanic isolator comprises:
- a first coupling unit connected to the at least one application connector; and
- a second coupling unit connected to the at least one supply connector,
- wherein the first coupling unit and the second coupling unit are configured to inductively and/or capacitively transmit electrical power from the at least one supply connector to the at least one application connector.

11. The medical apparatus according to claim 1, wherein a ratio v=d/L between a distance (d) between the at least one first radio unit and the at least one second radio unit and a wavelength (L) of the signals lies in a range of from 1.73 to 127.

12. The medical apparatus according to claim 1, wherein an area between the at least one first radio unit and the at least one second radio unit is at least partially filled with a material having a permittivity of from 1 to 23 F/m and has a conductivity of from 0 to 0.01 S/m.

13. The medical apparatus according to claim 1, wherein a radio path present between the first unit antenna and the second unit antenna has an extent of from 1 to 40 cm.

14. The medical apparatus according to claim 1, wherein: the first unit and the second unit antennas transmit the signals and/or data to each other across the visible distance.

15. The medical apparatus according to claim 14, wherein:
- the carrier is a single structure;
- the first unit and the second unit antennas are rigidly and solidly fixed on the single structure of the carrier.

16. The medical apparatus according to claim 1, wherein:
- the carrier is a single structure;
- the first unit and the second unit antennas are rigidly and solidly fixed on the single structure of the carrier.

* * * * *